United States Patent
Chang

(10) Patent No.: US 12,070,243 B2
(45) Date of Patent: Aug. 27, 2024

(54) MEDICAL MATERIAL NEEDLE

(71) Applicant: Industrial Technology Research Institute, Hsinchu (TW)

(72) Inventor: Chieh-Feng Chang, Changhua County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 357 days.

(21) Appl. No.: 17/477,584

(22) Filed: Sep. 17, 2021

(65) Prior Publication Data

US 2022/0096118 A1    Mar. 31, 2022

Related U.S. Application Data

(60) Provisional application No. 63/083,120, filed on Sep. 25, 2020.

(51) Int. Cl.
*A61B 17/34* (2006.01)

(52) U.S. Cl.
CPC ...... *A61B 17/3403* (2013.01); *A61B 17/3417* (2013.01); *A61B 2017/3413* (2013.01); *A61B 2017/3454* (2013.01)

(58) Field of Classification Search
CPC ............ A61B 17/3403; A61B 17/3417; A61B 2017/3413; A61B 2017/3454
See application file for complete search history.

(56) References Cited

U.S. PATENT DOCUMENTS

| | | | |
|---|---|---|---|
| 5,289,831 A | 3/1994 | Bosley | |
| 7,867,226 B2 | 1/2011 | Heim et al. | |
| 8,430,863 B2 * | 4/2013 | Webler | A61B 90/36 604/523 |
| 9,254,146 B2 | 2/2016 | Massengale et al. | |
| 9,445,837 B2 | 9/2016 | Fulton, III | |
| 9,717,552 B2 | 8/2017 | Cosman et al. | |

(Continued)

FOREIGN PATENT DOCUMENTS

| | | |
|---|---|---|
| CN | 103142294 A | 6/2013 |
| CN | 104162223 A | 11/2014 |

(Continued)

OTHER PUBLICATIONS

TW OA issued on Sep. 20, 2023.

(Continued)

*Primary Examiner* — Ashley L Fishback
(74) *Attorney, Agent, or Firm* — WPAT, P.C

(57) ABSTRACT

A medical material needle, applicable for detection and positioning by an ultrasound, includes a needle body having a three-layer structure. The three-layer structure includes an outer structure, an inner structure, and a middle structure disposed between the outer structure and the inner structure. The outer structure and the middle structure have different characteristic acoustic impedance with respect to the ultrasound, the inner structure and the middle structure have different characteristic acoustic impedance with respect to the ultrasound, and at least one of the outer structure, the middle structure and the inner structure is provided with a dimension in at least one direction less than a wavelength at a frequency of the ultrasound in water.

16 Claims, 11 Drawing Sheets

(56) References Cited

U.S. PATENT DOCUMENTS

| | | | |
|---|---|---|---|
| 9,782,565 | B2 | 10/2017 | McWeeney |
| 9,986,981 | B2 | 6/2018 | Schembre et al. |
| 2010/0239505 | A1 | 9/2010 | Reichl et al. |
| 2013/0190609 | A1 | 7/2013 | Fischer, Jr. |
| 2013/0211176 | A1 | 8/2013 | Habib |
| 2014/0257090 | A1 | 9/2014 | Fischer, Jr. et al. |
| 2015/0272542 | A1 | 10/2015 | Shuman et al. |
| 2015/0297092 | A1* | 10/2015 | Irisawa .............. A61B 5/06 600/407 |
| 2017/0049993 | A1 | 2/2017 | Cosman et al. |
| 2017/0050041 | A1 | 2/2017 | Cosman |
| 2017/0172618 | A1 | 6/2017 | Erkamp et al. |
| 2018/0344390 | A1 | 12/2018 | Brannan et al. |

FOREIGN PATENT DOCUMENTS

| | | |
|---|---|---|
| CN | 102860870 B | 9/2016 |
| CN | 105686866 B | 6/2019 |
| EP | 2462977 A1 | 6/2012 |
| TW | I572323 | 3/2017 |
| TW | I626035 B | 6/2018 |
| TW | I634868 B | 9/2018 |
| TW | I663271 B | 6/2019 |
| TW | 202023487 A | 7/2020 |

OTHER PUBLICATIONS

Diane Bergin et al., Echogenic Polymer Coating Does It Improve Needle Visualization in Sonographically Guided Biopsy, accepted after revision Oct. 30, 2001, May 2002, American Roentgen Ray Society, https://www.ajronline.org/doi/full/10.2214/ajr.178.5.1781188.

Simon Hebard et al., Echogenic Technology Can Improve Needle Visibility During Ultrasound-Guided Regional Anesthesia, Feb. 1, 2011, vol. 36, Issue 2, https://rapm.bmj.com/content/36/2/185-189.abstract.

TW OA issued on Feb. 17, 2022.

\* cited by examiner

MEDICAL MATERIAL NEEDLE

CROSS REFERENCE TO RELATED APPLICATION

This application claims the benefits of U.S. provisional application Ser. No. 63/083,120, filed Sep. 25, 2020, the disclosures of which are incorporated by references herein in its entirety.

TECHNICAL FIELD

This disclosure is related to a medical material needle, and more particularly to the medical material needle that can enhance echogenicity of ultrasound.

BACKGROUND

Due to tiny sizes of medical materials in clinical medicine such as needles, visibility of these materials under ultrasound imaging is usually too weak to be located.

Taking the radio-frequency thermal ablation electrode needle as an example, two common types of the radio-frequency thermal ablation needles, tine needles and straight needles, are usually seen in clinical practices.

In comparison with the straight needle, the tine needle can provide an ablation range that is closer to a spherical shape, and can also retain the flexibility in ablating irregular tumors. However, the individual tine needle is still too small to be clearly identified under ultrasound imaging.

Even for the straight needles with substantial diameters, if the needle diameter is below 19G (approximately equal to 1.07 mm), then identification of its ultrasound image becomes a problem.

In addition, a typical clinical method for confirming the tumor ablation range is usually to implant a temperature sensing device, such that a hyperechoic acupuncture device can be applied for ultrasound positioning of the temperature probe.

Although the needle can be coated with a specific material or produced to have concave surface structures to magnify ultrasound echo, yet, due to biocompatibility and conductivity that the puncture medical materials shall maintain for the ablation process, and to the necessity for easily removing the needle without contaminating any heated tissue after the ablation process, the aforesaid methods in coating or particular structuring may not be always suitable.

Accordingly, how to develop a "medical material needle" that can enhance the echogenicity of ultrasound, solve the problem of clinical needles and other fine medical materials that are difficult to locate under ultrasonic imaging, and keep the biocompatibility and conductivity at the outer layer of the needle is an urgent issue to the skill in the art.

SUMMARY

In one embodiment of this disclosure, a medical material needle, applicable to be detected and thus positioned by an ultrasound, including a needle body having a three-layer structure, the three-layer structure including:
   an outer structure;
   an inner structure; and
   a middle structure, disposed between the outer structure and inner structure;
   wherein the outer structure and the middle structure have different characteristic acoustic impedance with respect to the ultrasound, the inner structure and the middle structure have different characteristic acoustic impedance with respect to the ultrasound, and at least any of the outer structure, the middle structure and the inner structure has a dimension in at least one direction less than a wavelength at a frequency of the ultrasound in the water.

DETAILED DESCRIPTION

In this disclosure, a medical material needle is applicable to be detected and then positioned by an ultrasound. The medical material needle includes a needle body contained thereinside a three-layer structure for enhancing echogenicity with respect to the ultrasound, such that position detection can be easily carried out.

Figure 1:
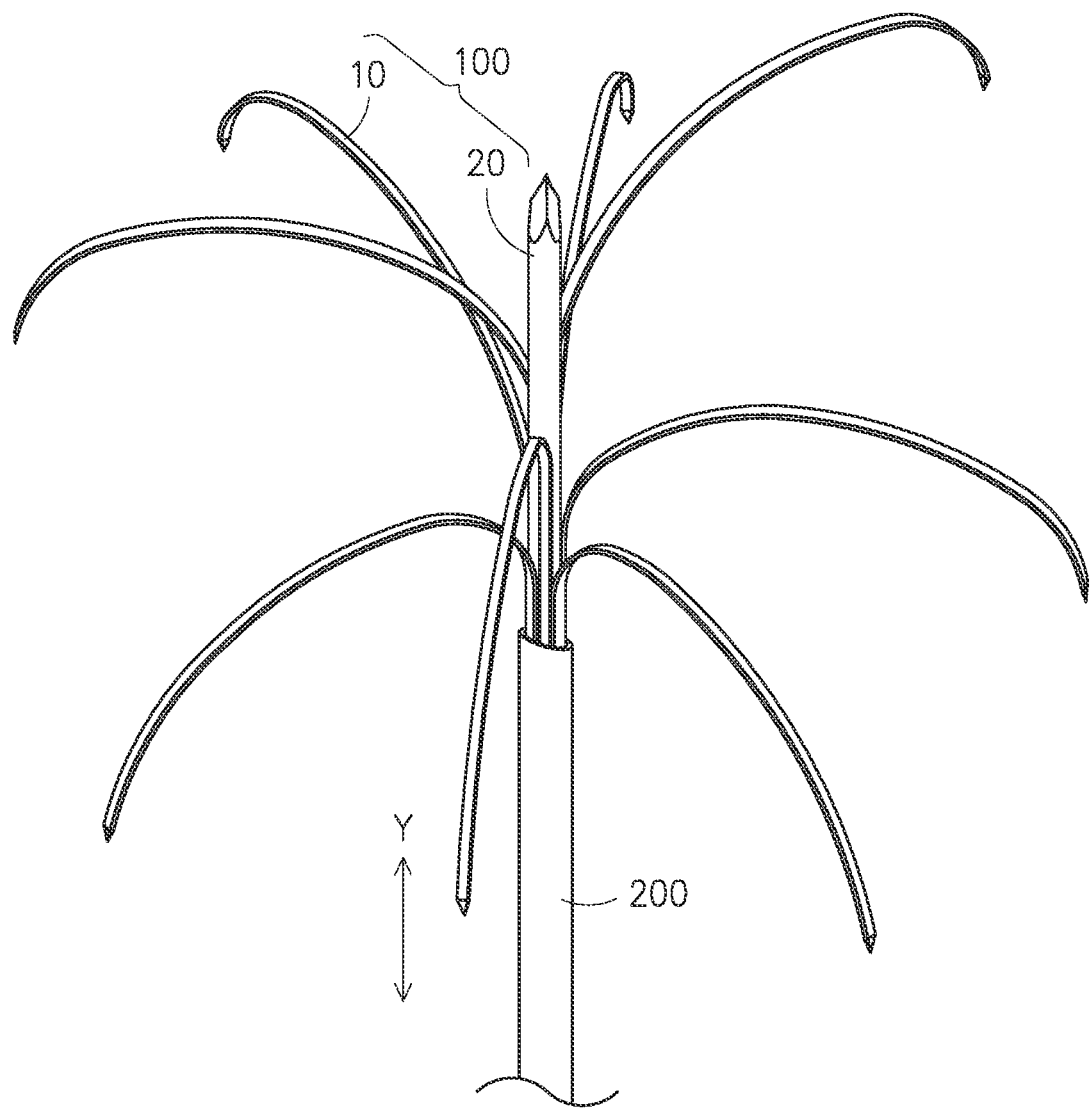
FIG. 1 is a schematic perspective view of a medical material needle in accordance with this disclosure.

Referring now to FIG. 1, in this embodiment, the medical material needle includes a needle body 100 with a three-layer structure and a guide pipe 200. The needle body 100 includes a plurality of tine needles 10 and a straight needle 20, in which the tine needles 10 are arranged to the outside of the straight needle 20 to surround the straight needle 20. Each of the tine needles 10 can be elastic and extend to bend in a radial direction of the straight needle 20. The guide pipe 200 can be made of a conducting material (for example, a conductive metal) or an insulation material, and configured to sleeve outside the needle body 100 (i.e., the tine needles 10 and the straight needle 20). In addition, the guide pipe 200 is movable axially in a Y direction for controlling the tine needles 10 to be retracted or expanded, such that exposing lengths of the tine needles 10 and the straight needle 20 can be adjusted.

The three-layer structure of the needle body 100 can be furnished to the tine needles 10 and/or the straight needle 20, but not limited thereto. In the following description, the three-layer structure provided to the tine needle 10 would be selected as the example in this disclosure.

Figure 2:
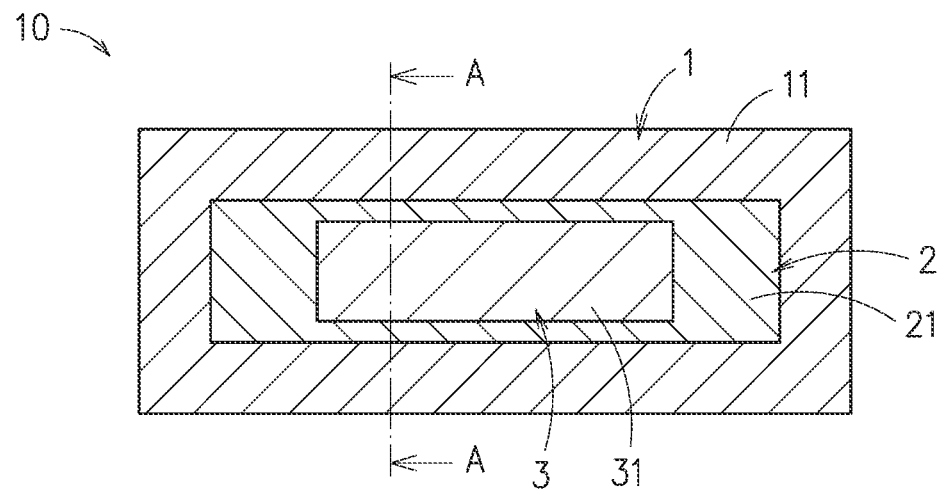
FIG. 2 is a schematic cross-sectional view of an embodiment of the tine needle.
Figure 2A:
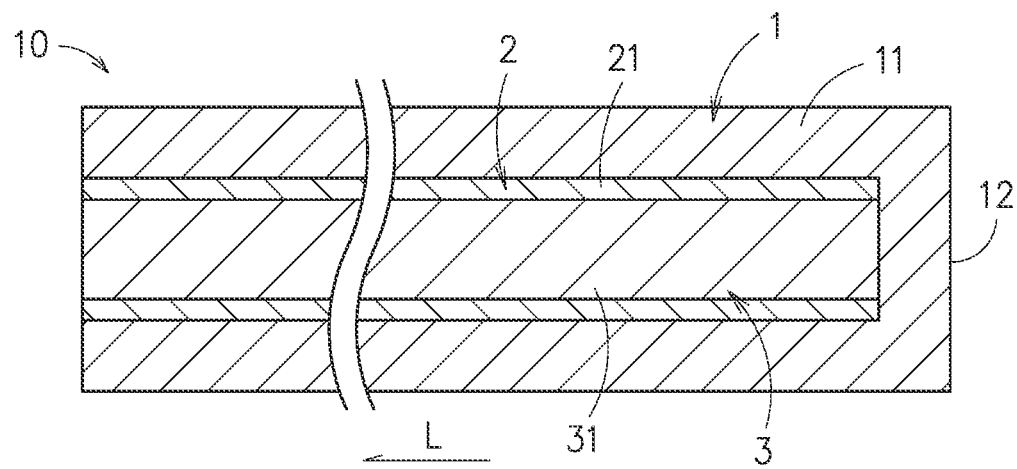
FIG. 2A is a schematic cross-sectional view of FIG. 2 along line A-A.

Referring now to FIG. 2 and FIG. 2A, the three-layer structure of the needle body 100 (see FIG. 1) is constructed at each or at least one of the tine needles 10. As shown, the tine needle 10 with a three-layer structure, formed to have a rectangular cross section, includes an outer structure 1, an inner structure 3 and a middle structure 2 disposed between the outer structure 1 and the inner structure 3. The outer structure 1 can provide the tine needle 10 at least one sealed end 12 in a longitudinal direction L of the tine needle 10, such that both the inner structure 3 and the middle structure 2 can be sealed inside the outer structure 1.

The outer structure 1 and the middle structure 2 can have different characteristic acoustic impedance with respect to the ultrasound. Similarly, the inner structure 3 and the middle structure 2 can have different characteristic acoustic impedance with respect to the ultrasound. In this disclosure, at least one of the outer structure 1, the middle structure 2 and the inner structure 3 is provided with a dimension in at least one direction less than a wavelength at a frequency of the ultrasound in water.

In one exemplary example, the characteristic acoustic impedance of each of the outer structure 1 and the inner structure 3 is larger than that of the middle structure 2, in which the outer structure 1 and the inner structure 3 may have the same or different characteristic acoustic impedance.

Further, in another exemplary example, the characteristic acoustic impedance of each of the outer structure 1 and the inner structure 3 is less than that of the middle structure 2, in which the outer structure 1 and the inner structure 3 may have the same or different characteristic acoustic impedance; but, not limited thereto.

In this disclosure, the characteristic acoustic impedance can be defined by an equation as follows:

Characteristic acoustic impedance=Material density× Acoustic speed in material

Generally speaking, a high value of the characteristic acoustic impedance can be larger than $1 \times 10^7$ rayl, and a low value of the characteristic acoustic impedance can be lower than $5 \times 10^6$ rayl. A list of the characteristic acoustic impedance of different materials is provided as follows.

| Classification of characteristic acoustic impedance | Material | Characteristic acoustic impedance (rayl) |
| --- | --- | --- |
| High | Tungsten (W) | ~$8.0 \times 10^7$ |
|  | Platinum (Pt) | ~$5.8 \times 10^7$ |
|  | Stainless steel 304 | ~$4.0 \times 10^7$ |
|  | Copper (Cu) | ~$3.1 \times 10^7$ |
|  | Titanium (Ti) | ~$2.3 \times 10^7$ |
|  | Aluminum (Al) | ~$1.4 \times 10^7$ |

-continued

| Classification of characteristic acoustic impedance | Material | Characteristic acoustic impedance (rayl) |
| --- | --- | --- |
| Low | Polylactide | ~$3.0 \times 10^6$ |
|  | Polyurethane | ~$1.9 \times 10^6$ |
|  | Polystyrene | ~$1.9 \times 10^6$ |
|  | Polyethylene | ~$1.7 \times 10^6$ |
|  | Water | ~$1.5 \times 10^6$ |
|  | Air | ~412 |

In FIG. 2, the outer structure 1 includes a first material 11, the middle structure 2 includes a second material 21, and the inner structure 3 includes a third material 31. The second material 21 of the middle structure 2 is to wrap the third material 31 of the inner structure 3, and the first material 11 of the outer structure 1 is to wrap the second material 21 of the middle structure 2.

In one exemplary embodiment, the first material 11 is stainless steel, the second material 21 is polystyrene, and the third material 31 is copper (Cu). Namely, in this example, each of the outer structure 1 and the inner structure 3 has the characteristic acoustic impedance higher than the middle structure 2 does, and the outer structure 1 and the inner structure 3 have different characteristic acoustic impedance.

In another exemplary embodiment, the first material 11 is stainless steel, the second material 21 is polystyrene, and the third material 31 is also stainless steel. Namely, in this example, each of the outer structure 1 and the inner structure 3 has the characteristic acoustic impedance higher than the middle structure 2 does, and the outer structure 1 and the inner structure 3 have the same characteristic acoustic impedance.

In a further exemplary embodiment, the first material 11 is polystyrene, the second material 21 is copper (Cu), and the third material 31 is polystyrene. Namely, in this example, each of the outer structure 1 and the inner structure 3 has the characteristic acoustic impedance less than the middle structure 2 does, and the outer structure 1 and the inner structure 3 have the same characteristic acoustic impedance.

In one more exemplary embodiment, the first material 11 is polystyrene, the second material 21 is copper (Cu), and the third material 31 is polyurethane. Namely, in this example, each of the outer structure 1 and the inner structure 3 has the characteristic acoustic impedance less than the middle structure 2 does, and the outer structure 1 and the inner structure 3 have different characteristic acoustic impedance.

Nevertheless, choices of the first material 11, the second material 21 and the third material 31 are not limited to the materials listed in the foregoing table. For example, in some other examples, the first material 11 may be a metal, a conducting material, a thermoelectric material or a solid material with biocompatibility, and the second material 21 or the third material 31 may be a metal or a polymer.

In addition, in one exemplary example, any two neighboring layers (i.e., the outer structure 1 and the middle structure 2, or the middle structure 2 and the inner structure 3) have a difference of the characteristic acoustic impedance more than $2.0 \times 10^6$ rayl, or a percentage difference of the characteristic acoustic impedance more than 20%; but, not limited thereto.

Figure 3:
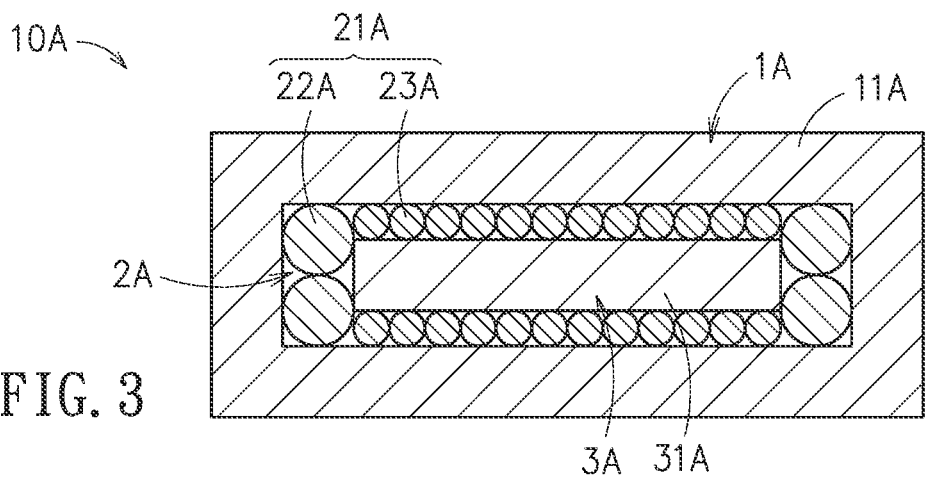
FIG. 3 is another schematic cross-sectional view of the tine needle.

Referring now to another embodiment shown in FIG. 3, the medical material needle includes a needle body 100 (see FIG. 1) having a three-layer structure. The needle body 100 includes a plurality of tine needles 10A, and each of the tine needles 10A has a rectangular cross section structured to provide the three-layer structure. As shown, the three-layer structure includes an outer structure 1A, an inner structure 3A and a middle structure 2A, in which the middle structure 2A is disposed between the outer structure 1A and the inner structure 3A.

The outer structure 1A and the middle structure 2A can have different characteristic acoustic impedance with respect to the ultrasound. Similarly, the inner structure 3A and the middle structure 2A can have different characteristic acoustic impedance with respect to the ultrasound. In this disclosure, at least one of the outer structure 1A, the middle structure 2A and the inner structure 3A is provided with a dimension in at least one direction less than a wavelength at a frequency of the ultrasound in water.

The outer structure 1A includes a first material 11A, the middle structure 2A includes a second material 21A, and the inner structure 3A includes a third material 31A. The second material 21A of the middle structure 2A is partly adhered to the third material 31A of the inner structure 3A, and the second material 21A of the middle structure 2A is to wrap the third material 31A of the inner structure 3A, and the first material 11A of the outer structure 1A is to wrap the second material 21A of the middle structure 2A.

Figure 3A:
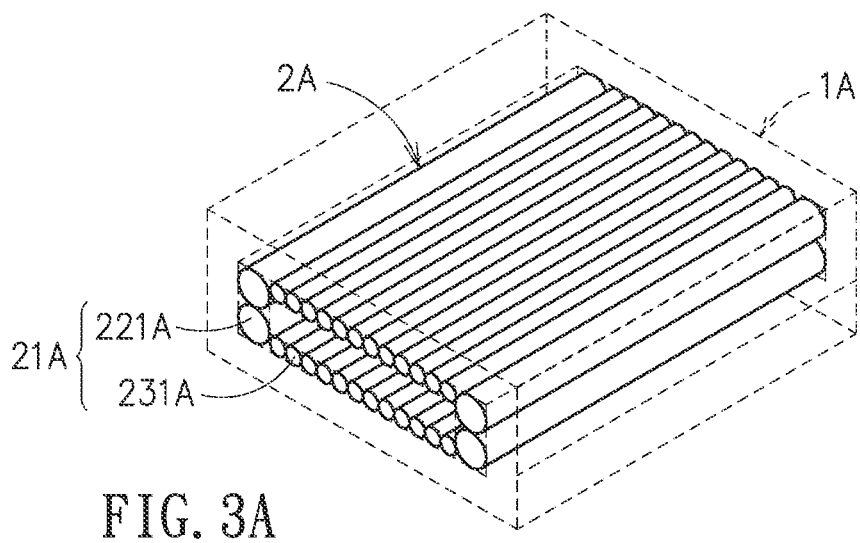
FIGS. 3A~3B show schematically different exemplary examples for FIG. 3.
Figure 3B:
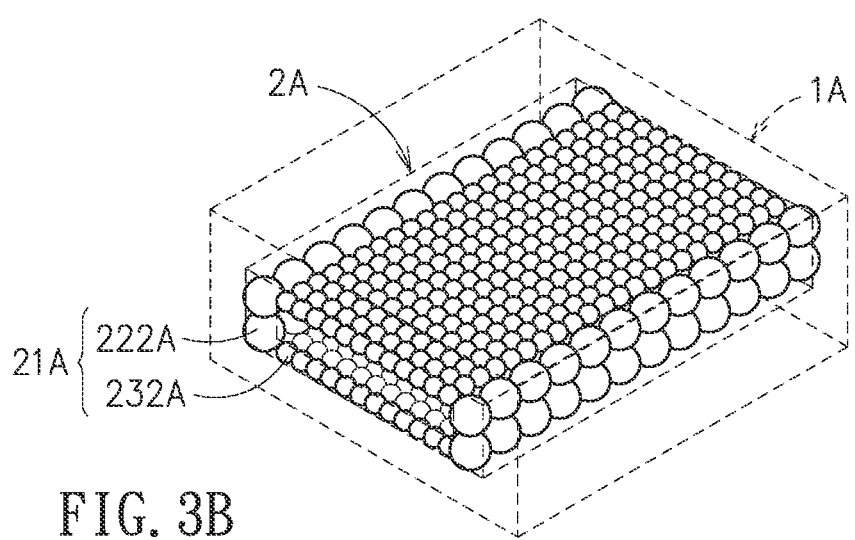

It shall be noted that, in FIG. 2, the second material 21A of the middle structure 2A is consisted of two different structural units 22A, 23A. Referring to FIG. 3A and FIG. 3B, two different exemplary examples for the second material 2A of FIG. 3 are provided.

Referring to FIG. 3A, the second material 21A of the middle structure 2A includes a plurality of cylindrical structural units 221A, 231A in a predetermined arrangement, in which the cylindrical structural unit 221A and the cylindrical structural unit 231A have different diameters, and the second material 21A of the middle structure 2A is arranged to wrap the inner structure 3A.

Referring to FIG. 3B, the second material 21A of the middle structure 2A is consisted of a plurality of granular structural units 222A, 232A in a predetermined arrangement, in which the granular structural unit 222A and the granular structural unit 232A have different diameters, and the second material 21A of the middle structure 2A is arranged to wrap the inner structure 3A.

In the following description, various exemplary examples (FIGS. 4A~4C, 5A~5C) derived from FIG. 3 are provided.

Figure 4A:
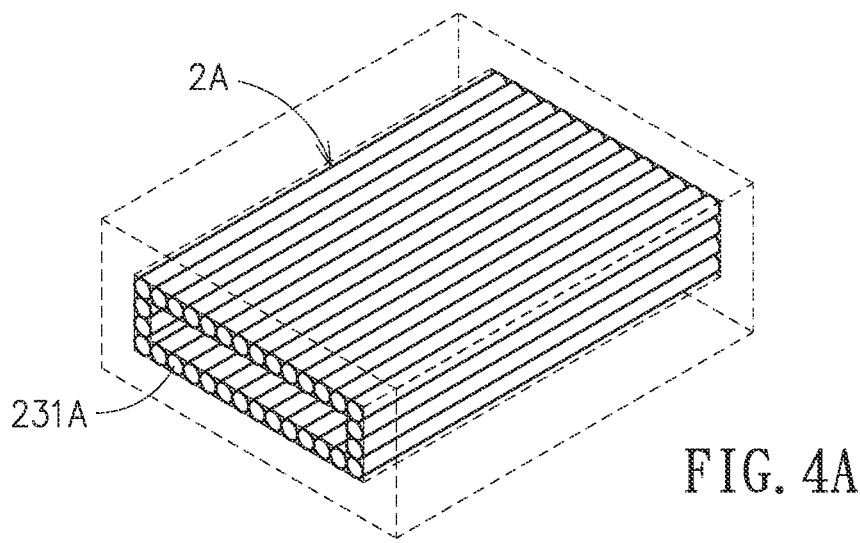
FIGS. 4A~C show schematically different exemplary examples for the arrangement of the cylindrical structural units for the middle structure.

Referring now to FIG. 4A, the middle structure 2A includes a plurality of cylindrical structural units 231A with the same diameter and in a single-layer arrangement.

Figure 4B:
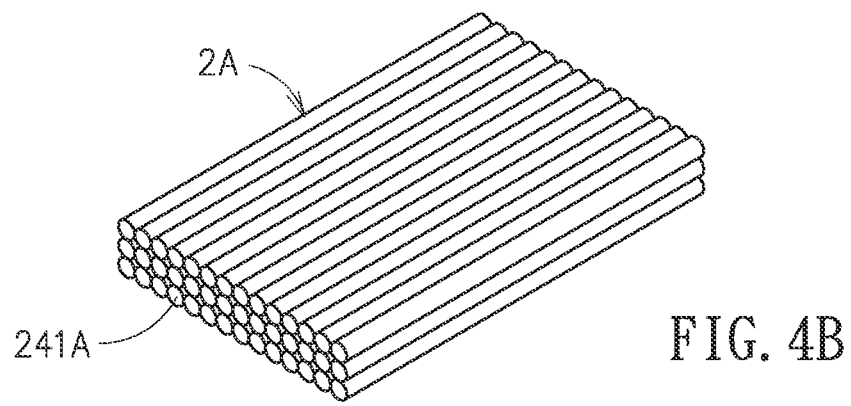

Referring now to FIG. 4B, the middle structure 2A includes a plurality of cylindrical structural units 241A with the same diameter but in a cubic multi-layer arrangement. In addition, the arrangement in FIG. 4B can be regular (as shown) or irregular.

Figure 4C:
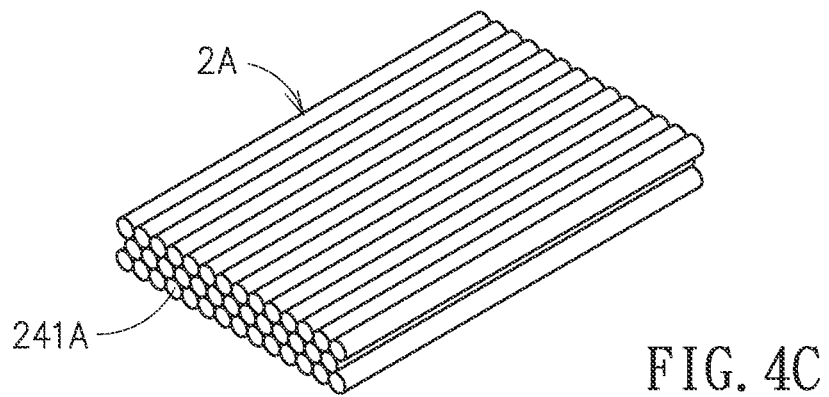

Referring now to FIG. 4C, the middle structure 2A includes a plurality of cylindrical structural units 241A with the same diameter but in a hexagonal multi-layer arrangement. In addition, the arrangement in FIG. 4C can be regular (as shown) or irregular.

It shall be noted that only a part of the middle structure 2A is shown in FIG. 4B or 4C. That is, the single-layer arrangement of the cylindrical structural units 231A in FIG. 4A can be replaced by the cubic or hexagonal multi-layer arrangement of the cylindrical structural units 241A in FIG. 4B or 4C, respectively.

Figure 5A:
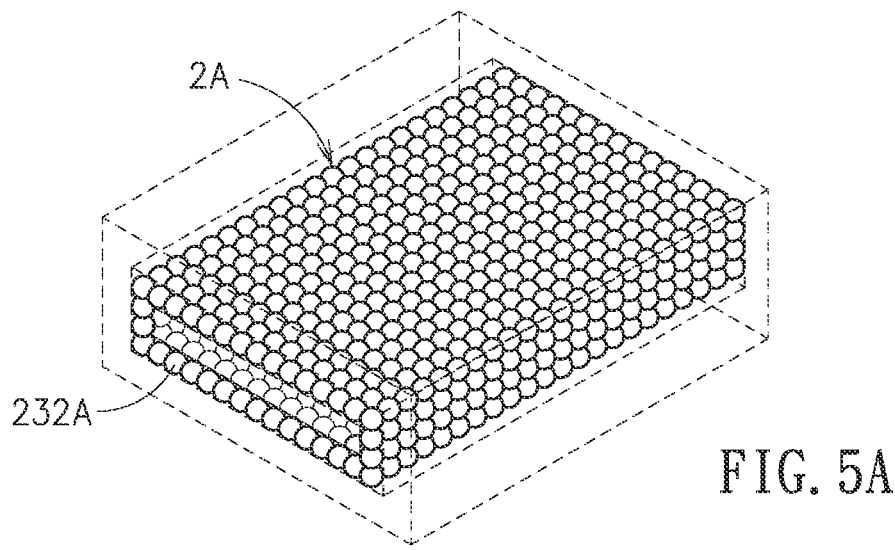
FIGS. 5A~5C show schematically different exemplary examples of the arrangement of the granular structural units for the middle structure.

Referring to FIG. 5A, the middle structure 2A includes a plurality of granular units 232A with the same diameter and in a single-layer arrangement.

Figure 5B:
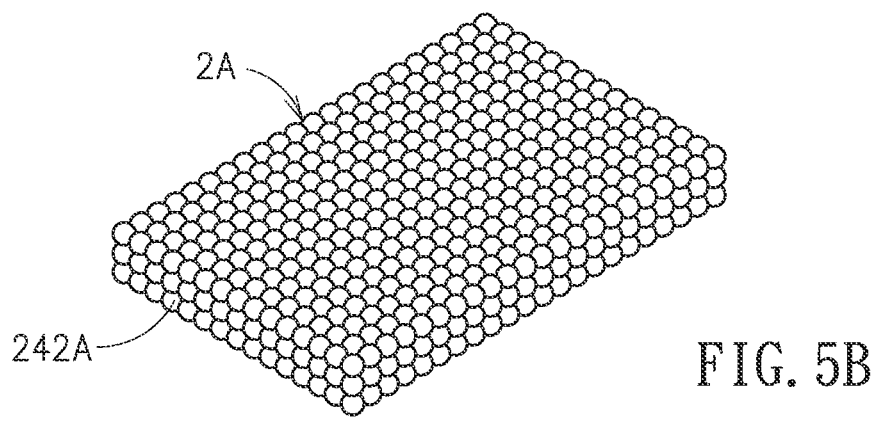

Referring now to FIG. 5B, the middle structure 2A includes a plurality of granular structural units 242A with the same diameter but in a cubic multi-layer arrangement. In addition, the arrangement in FIG. 5B can be regular (as shown) or irregular.

Figure 5C:
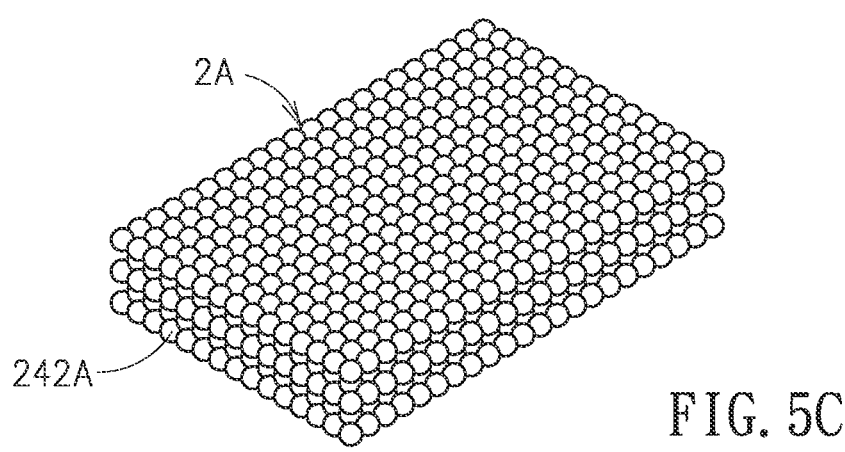

Referring now to FIG. 5C, the middle structure 2A includes a plurality of granular structural units 242A with the same diameter but in a hexagonal multi-layer arrangement. In addition, the arrangement in FIG. 5C can be regular (as shown) or irregular.

It shall be noted that only a part of the middle structure 2A is shown in FIG. 5B or 5C. That is, the single-layer arrangement of the granular structural units 232A in FIG. 5A can be replaced by the cubic or hexagonal multi-layer arrangement of the granular structural units 242A in FIG. 5B or 5C, respectively.

From the aforesaid examples shown in FIG. 3 through FIG. 5C, it is understood that, according to this disclosure, the middle structure can be consisted of a plurality of structural units with different shapes, dimensions, arrangements (either regular or irregular), such as the aforesaid cylindrical structural units 221A, 231A, 241A, or the aforesaid granular structural units 222A, 232A, 242A. According to this disclosure, the cylindrical structural units 221A, 231A, 241A, and the granular structural units 222A, 232A, 242A can be applied in any combination, and the materials for producing the same can be identical or different to each other.

Figure 6:
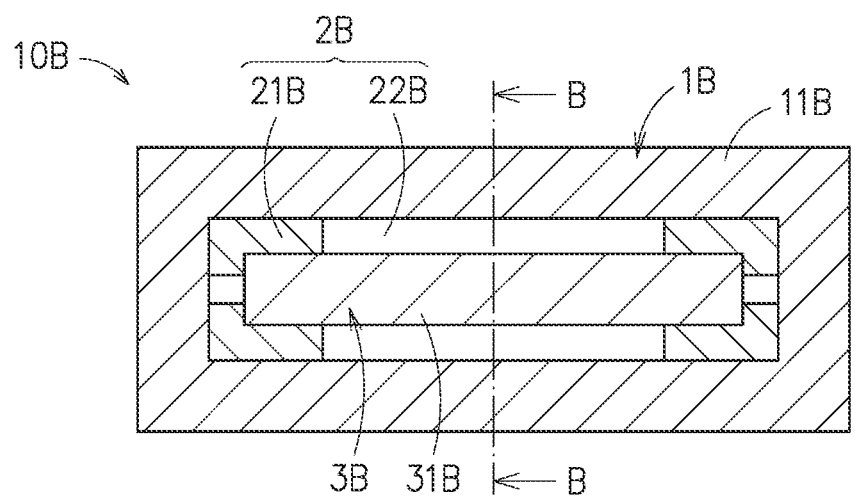
FIG. 6 is a schematic cross-sectional view of another embodiment of the tine needle.
Figure 6A:
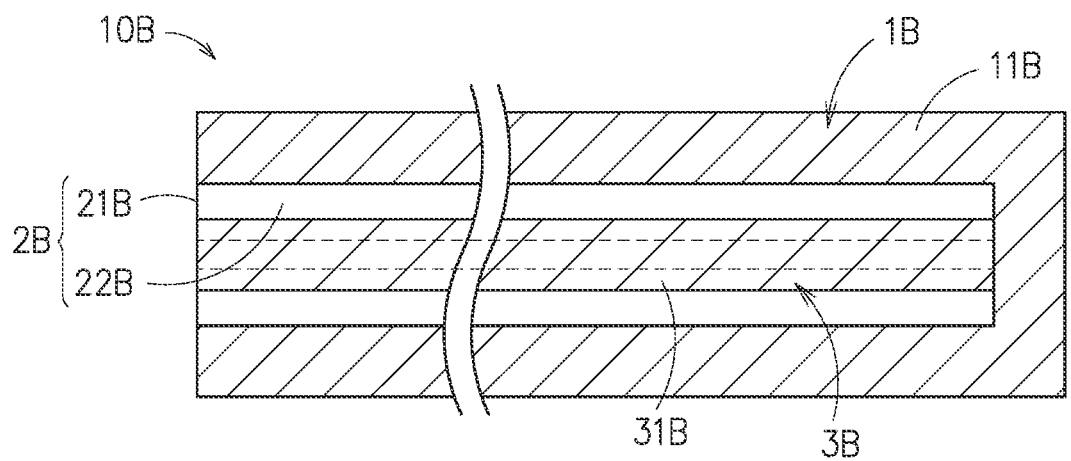
FIG. 6A is a schematic cross-sectional view of FIG. 6 along line B-B.

Referring to FIG. 6 and FIG. 6A, in this embodiment, the medical material needle includes a needle body 100 having a three-layer structure (see FIG. 1) includes a plurality of tine needles 10B. As shown, the tine needle 10B with the three-layer structure, formed to have a rectangular cross section, includes an outer structure 1B, an inner structure 3B and a middle structure 2B disposed between the outer structure 1B and the inner structure 3B.

The outer structure 1B and the middle structure 2B can have different characteristic acoustic impedance with respect to the ultrasound. Similarly, the inner structure 3B and the middle structure 2B can have different characteristic acoustic impedance with respect to the ultrasound. In this embodiment, at least one of the outer structure 1B, the middle structure 2B and the inner structure 3B is provided with a dimension in at least one direction less than a wavelength at a frequency of the ultrasound in water.

The outer structure 1B includes a first material 11B, the middle structure 2B includes a second material 21B and a fourth material 22B, and the inner structure 3B includes a third material 31B. In detail, the second material 21B and the fourth material 22B are disposed in an alternative manner. The second material 21B of the middle structure 2B is to cover part of the third material 31B of the inner structure 3B, and the fourth material 22B of the middle structure 2B is to cover the rest part of the third material 31B of the inner structure 3B. Namely, the second material 21B and the fourth material 22B are integrated, but in an alternative manner, to wrap the third material 31B of the inner structure 3B. In addition, the first material 11B of the outer structure 1B is to wrap both the second material 21B and the fourth material 22B of the middle structure 2B. According to this disclosure, the fourth material 22B can be a solid material such as a metal or a polymer, or a fluid such as water, air or the like gas or fluid.

Figure 7:
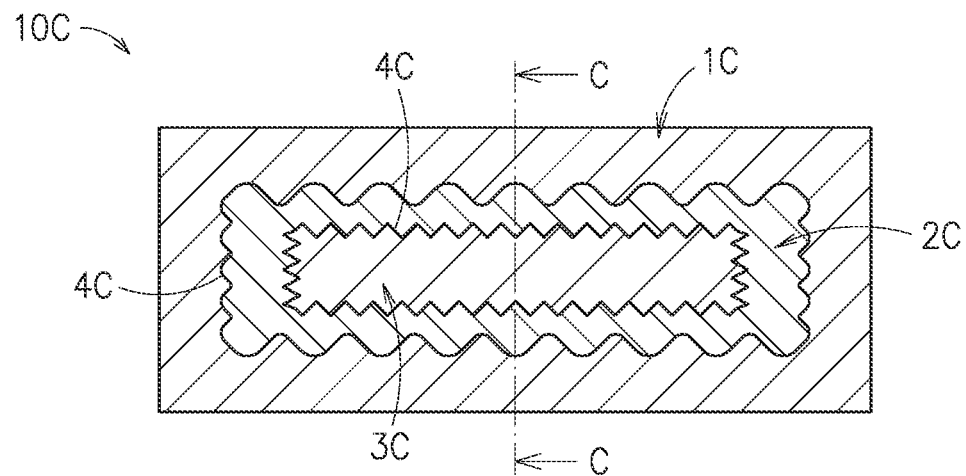
FIG. 7 is a schematic cross-sectional view of a further embodiment of the tine needle.
Figure 7A:
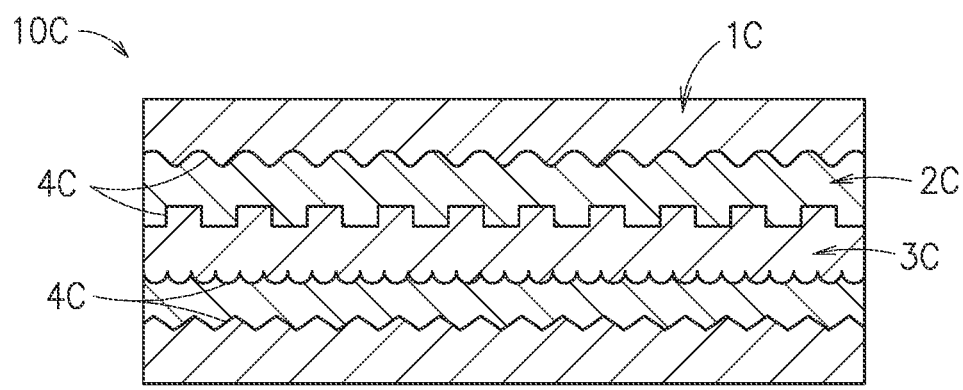
FIG. 7A is a schematic cross-sectional view of FIG. 7 along line C-C.

Referring now to FIG. 7 and FIG. 7A, in this embodiment, the medical material needle includes a needle body 100 having a three-layer structure (see FIG. 1) and the needle body 100 includes a plurality of tine needles 10C. As shown, the tine needle 10C with the three-layer structure, formed to have a rectangular cross section, includes an outer structure 1C, an inner structure 3C and a middle structure 2C disposed between the outer structure 1C and the inner structure 3C.

The outer structure 1C and the middle structure 2C can have different characteristic acoustic impedance with respect to the ultrasound. Similarly, the inner structure 3C and the middle structure 2C can have different characteristic acoustic impedance with respect to the ultrasound. In this embodiment, at least one of the outer structure 1C, the middle structure 2C and the inner structure 3C is provided with a dimension in at least one direction less than a wavelength at a frequency of the ultrasound in water.

It shall be noted that, in this embodiment, a contact surface between the outer structure 1C and the middle structure 2C, and another contact surface between the middle structure 2C and the inner structure 3C are both formed to include micro structures 4C.

According to this disclosure, dimensions and shapes of the micro structures 4C may be the same or different, but determined per practical requirements. It shall be noted that the micro structures 4C of FIG. 7A are not configured to resemble the micro structures 4C of FIG. 7. Such a variation is simple to claim that the micro structures 4C of this disclosure can be versatilely configured. Definitely, the configuration of the micro structures 4C may purposely meet practical needs to construct at the contact surface between the outer structure 1C and the middle structure 2C, but none at the contact surface between the middle structure 2C and the inner structure 3C; and vice versa.

In one embodiment of this disclosure, a medical material needle may include a needle body having a three-layer structure, and the needle body simply includes a straight needle 20. The three-layer structure is constructed at the straight needle 20.

Figure 8:
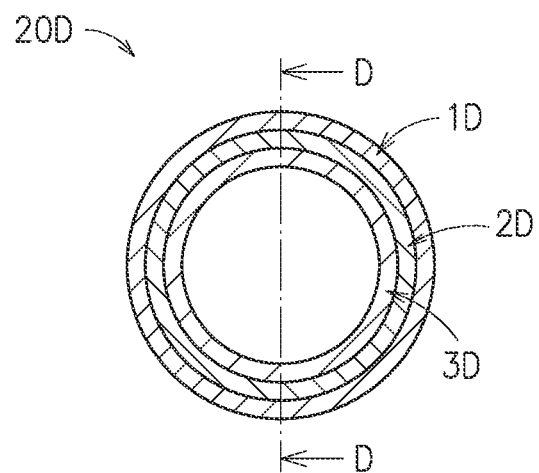
FIG. 8 is a schematic cross-sectional view of an embodiment of the straight needle.
Figure 8A:
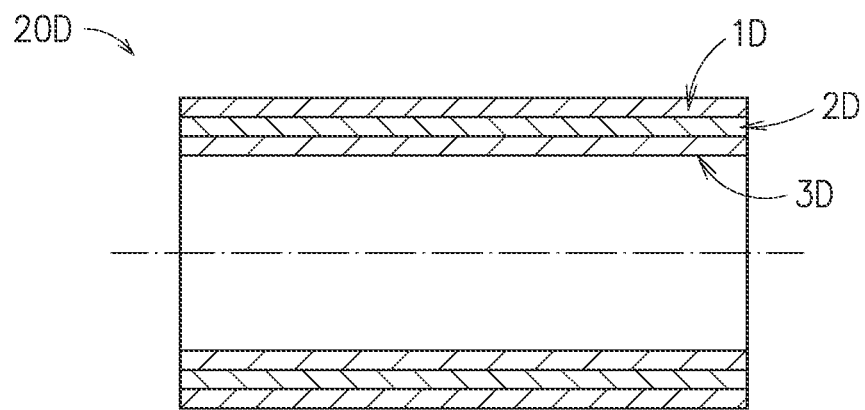
FIG. 8A is a schematic cross-sectional view of FIG. 8 along line D-D.

Referring to FIG. 8 and FIG. 8A, a medical material needle includes a needle body 100 having a three-layer structure (see FIG. 1). The needle body 100 includes a straight needle 20D furnished with the three-layer structure. As shown, the straight needle 20D having a circular cross section includes an outer structure 1D, an inner structure 3D and a middle structure 2D, in which the middle structure 2D is disposed between the outer structure 1D and the inner structure 3D. In this embodiment, the inner structure 3D is formed as a hollow cylindrical structure for allowing a fluid to flow thereinside or a wire to pass therethrough.

The outer structure 1D and the middle structure 2D can have different characteristic acoustic impedance with respect to the ultrasound. Similarly, the inner structure 3D and the middle structure 2D can have different characteristic acoustic impedance with respect to the ultrasound. In this disclosure, at least one of the outer structure 1D, the middle structure 2D and the inner structure 3D is provided with a dimension in at least one direction less than a wavelength at a frequency of the ultrasound in water.

Figure 9:
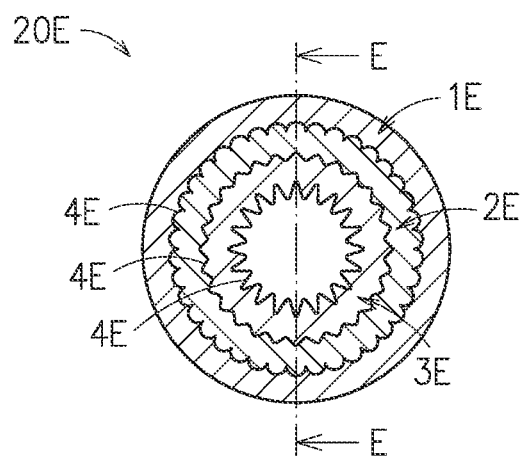
FIG. 9 is a schematic cross-sectional view of another embodiment of the straight needle.
Figure 9A:
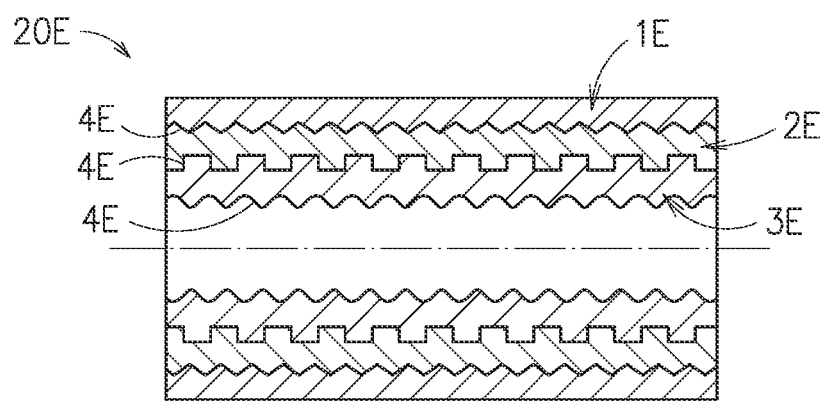
FIG. 9A is a schematic cross-sectional view of FIG. 9 along line E-E.

Referring to FIG. 9 and FIG. 9A, a medical material needle includes a needle body 100 having a three-layer structure (see FIG. 1). The needle body 100 includes a straight needle 20E furnished with the three-layer structure. As shown, the straight needle 20E having a circular cross section includes an outer structure 1E, an inner structure 3E and a middle structure 2E, in which the middle structure 2E is disposed between the outer structure 1E and the inner structure 3E. In this embodiment, the inner structure 3E is formed as a hollow cylindrical structure for allowing a fluid to flow thereinside or a wire to pass therethrough.

The outer structure 1E and the middle structure 2E can have different characteristic acoustic impedance with respect to the ultrasound. Similarly, the inner structure 3E and the middle structure 2E can have different characteristic acoustic impedance with respect to the ultrasound. In this disclosure, at least one of the outer structure 1E, the middle structure 2E and the inner structure 3E is provided with a dimension in at least one direction less than a wavelength at a frequency of the ultrasound in water.

In this embodiment, a contact surface between the outer structure 1E and the middle structure 2E, and another contact surface between the middle structure 2E and the inner structure 3E are both formed to include micro structures 4E. Dimensions and shapes of the micro structures 4E may be the same or different, but determined per practical requirements. It shall be noted that the micro structures 4E of FIG. 9A are not configured to resemble the micro structures 4E of FIG. 9. Such a variation is simple to claim that the micro structures 4E of this disclosure can be versatilely configured. Definitely, the configuration of the micro structures 4E may purposely meet practical needs to construct at the contact surface between the outer structure 1E and the middle structure 2E, but none at the contact surface between the middle structure 2E and the inner structure 3E; and vice versa.

In the aforesaid embodiments, the tine needle of the needle body 100 (see FIG. 1) has a rectangular cross section, while the straight needle thereof is a circular cross section. However, according to this disclosure, shapes of both the aforesaid cross sections are not limited thereto. In some other embodiments, the tine needle may have a circular cross section, and the straight needle may have a rectangular cross section. In particular, the tine needle and/or the straight needle may have a cross section formed to the other shape not listed herein.

Figure 10:
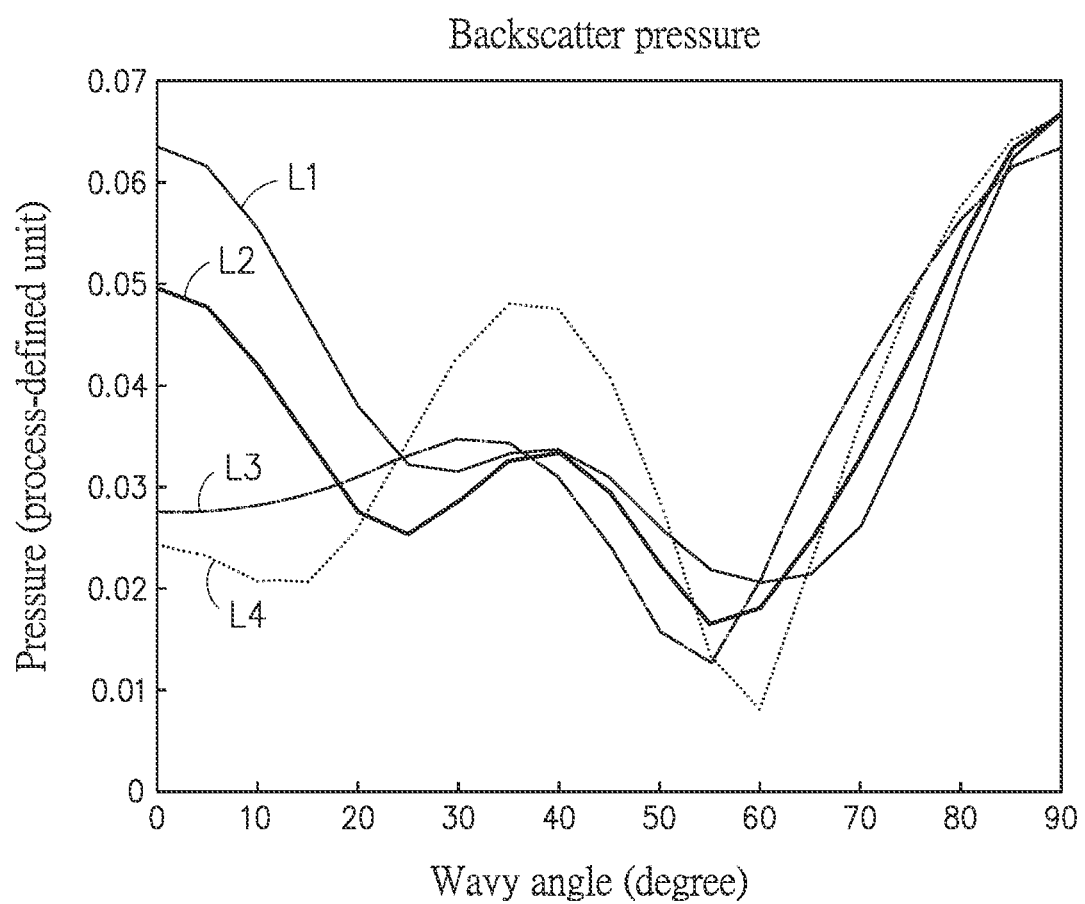
FIG. 10 demonstrates schematically simulation results in echo effects for different-material examples of the three-layer needle body of FIG. 2, an example of the two-layer needle body, and an example of the solid single-layer needle body.

Referring now to FIG. 10, simulation results in echo effects for different-material examples of the three-layer needle body of FIG. 2, an example of the two-layer needle body, and an example of the solid single-layer needle body are demonstrated schematically. In this illustration, curves L1~L4 all have the same dimensions for the needle bodies, but different materials and structures therefor.

In FIG. 10, curve L1 is corresponding to an example of FIG. 2, in which the first material 11 of the outer structure 1 is stainless steel, the second material 21 of the middle structure 2 is polystyrene, and the third material 31 of the inner structure 3 is copper (Cu); and, curve L2 is corresponding to another example of FIG. 2, in which the first material 11 of the outer structure 1 is stainless steel, the second material 21 of the middle structure 2 is polystyrene, and the third material 31 of the inner structure 3 is stainless steel. On the other hand, curve L3 is corresponding to a reference example having a two-layer needle body, in which the outer layer of the needle body is stainless steel, and the inner layer thereof is air; and, curve L4 is corresponding to another reference example having a solid single-layer needle body made of stainless steel. The simulations of echo effects to these four needle bodies are performed by giving the same 3 MHz ultrasound. In FIG. 10, the horizontal X axis is the wavy angle standing for the incidence angle of the ultrasound with respect to the needle body. In this testing, the incidence angle perpendicular to the long-side direction of the rectangular cross section of the tine needle 10 is 90°, while the incidence angle perpendicular to the short-side direction thereof is 0°.

As shown in FIG. 10, curves L1, L2 demonstrate good echo effects with respect to the given ultrasound. It implies that the three-layer structure provided in this disclosure can be clearly identified within the applied frequency band of the ultrasound. Namely, positioning of the needle body can be much easier.

Figure 11:
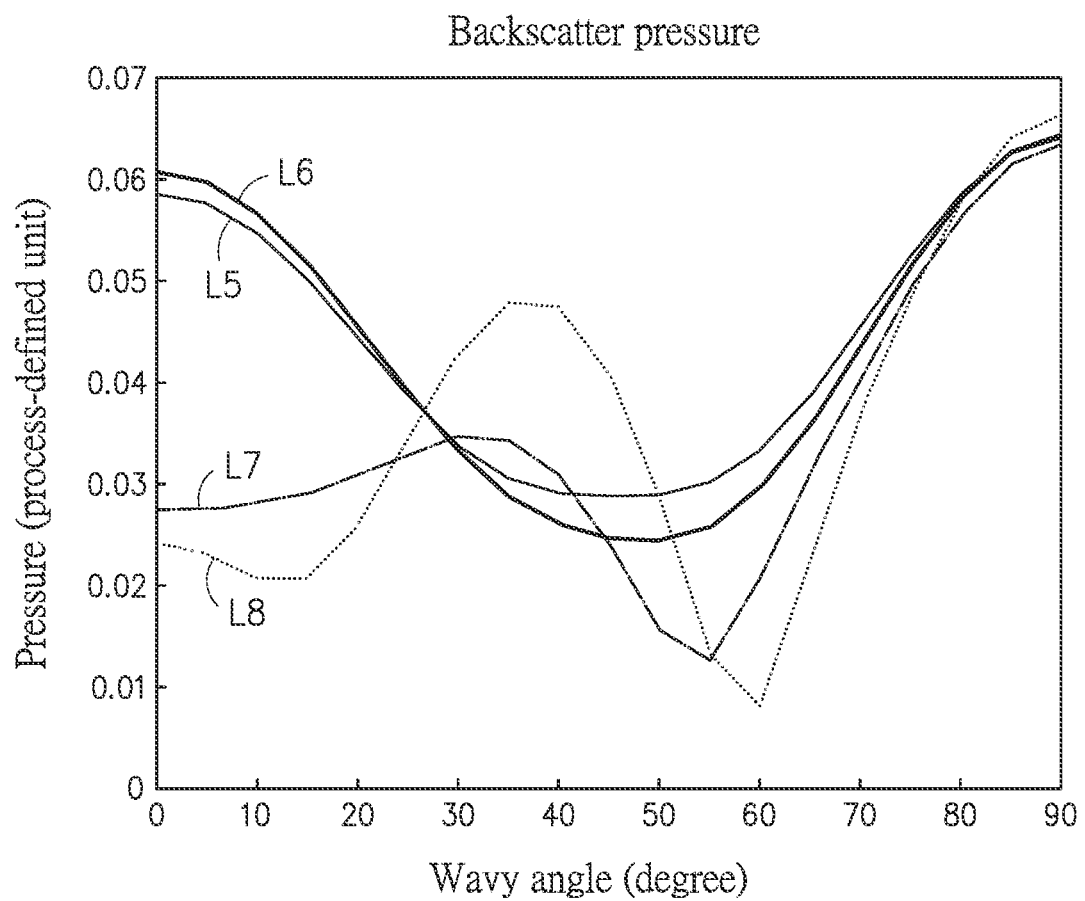
FIG. 11 demonstrates schematically simulation results in echo effects for different-material examples of the three-layer needle body of FIG. 6, an example of the two-layer needle body, and an example of the solid single-layer needle body.

Referring now to FIG. 11, simulation results in echo effects for different-material examples of the three-layer needle body of FIG. 6, an example of the two-layer needle body, and an example of the solid single-layer needle body are demonstrated schematically. In this illustration, curves L5~L8 all have the same dimensions for the needle bodies, but different materials and structures therefor.

In FIG. 11, curve L5 is corresponding to an example of FIG. 6, in which the first material 11B of the outer structure 1B is stainless steel, the second and fourth materials 21B, 22B of the middle structure 2B are respectively polystyrene and air, and the third material 31B of the inner structure 3B is copper (Cu); and, curve L6 is corresponding to another example of FIG. 6, in which the first material 11B of the outer structure 1B is stainless steel, the second and fourth materials 21B, 22B of the middle structure 2B are respectively polystyrene and air, and the third material 31B of the inner structure 3B is stainless steel. On the other hand, curve L7 is corresponding to a reference example having a two-layer needle body, in which the outer layer of the needle body is stainless steel, and the inner layer thereof is air; and, curve L8 is corresponding to another reference example having a solid single-layer needle body made of stainless steel. The simulations of echo effects to these four needle bodies are performed by giving the same 3 MHz ultrasound. In FIG. 11, the horizontal X axis is the wavy angle standing for the incidence angle of the ultrasound with respect to the needle body. In this testing, the incidence angle perpendicular to the long-side direction of the rectangular cross section of the tine needle 10 is 90°, while the incidence angle perpendicular to the short-side direction thereof is 0°.

As shown in FIG. 11, curves L5, L6 demonstrate good echo effects with respect to the given ultrasound. It implies that the three-layer structure provided in this disclosure can be clearly identified within the applied frequency band of the ultrasound. Namely, positioning of the needle body can be much easier.

From FIG. 10 and FIG. 11, it can be understood that the three-layer medical material needles according to this disclosure can provide superior echo effects to the conventional solid single-layer needle or the two-layer needle. That is, it is proved that the three-layer medical material needle provided in this disclosure can enhance significantly the echogenicity with respect to the ultrasound. As such, position identification upon the medical material needle by the ultrasound can be performed much more conveniently and easily.

In summary, with the medical material needle provided in this disclosure to include the needle body having the three-layer structure, versatile material selections can be applied to the outer structure, the inner structure and the middle structure of the three-layer structure, such that the outer structure and the middle structure can have different characteristic acoustic impedance with respect to the ultrasound, also the inner structure and the middle structure can have different characteristic acoustic impedance with respect to the ultrasound, and at least one of the outer structure, the middle structure and the inner structure can be provided with a dimension in at least one direction less than a wavelength at a frequency of the ultrasound in water. The three-layer structure of the needle body in this disclosure is applicable to the straight needle or the tine needle, either hollow or solid structure. Thereupon, the echogenicity with respect to the ultrasound can be enhanced, so that the conventional shortcoming in positioning the tiny medical material (such as the needle) by the ultrasound clinically can be substantially resolved. In addition, by keeping the same smoothness and materials for the needle, the biocompatibility and the electrical conductivity at the outer layer of the needle can be maintained, and thus the shortcoming in tissue adhesion after the ablation process can be much improved.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A medical material needle, adapted for detection and positioning by an ultrasound, the medical material needle including a needle body having a three-layer structure, the three-layer structure comprising:
   an outer structure;
   an inner structure; and
   a middle structure, disposed between the outer structure and the inner structure;
   wherein the outer structure and the middle structure have different characteristic acoustic impedance with respect to the ultrasound, the inner structure and the middle structure have different characteristic acoustic impedance with respect to the ultrasound, and at least one of the outer structure, the middle structure and the inner structure is provided with a dimension in at least one direction less than a wavelength at a frequency of the ultrasound in water.

2. The medical material needle of claim 1, wherein the characteristic acoustic impedance of the outer structure and that of the inner structure are both higher than that of the middle structure, and the characteristic acoustic impedance of the outer structure and that of the inner structure is either the same or different.

3. The medical material needle of claim 1, wherein the characteristic acoustic impedance of the outer structure and that of the inner structure are both lower than that of the middle structure, and the characteristic acoustic impedance of the outer structure and that of the inner structure is either the same or different.

4. The medical material needle of claim 1, wherein a difference of the characteristic acoustic impedance between the outer structure and the middle structure, or between the middle structure and the inner structure is over $2.0 \times 10^6$ rayl.

5. The medical material needle of claim 1, wherein a percentage difference of the characteristic acoustic impedance between the outer structure and the middle structure, or between the middle structure and the inner structure is over 20%.

6. The medical material needle of claim 1, wherein the outer structure includes a first material, the middle structure includes a second material, the inner structure includes a third material, the third material of the inner structure is wrapped by the second material of the middle structure, and the second material of the middle structure is wrapped by the first material of the outer structure.

7. The medical material needle of claim 6, wherein the first material includes a metal, a conducting material, a thermoelectric material or a solid material with biocompatibility, and either the second material or the third material includes a metal or a polymer.

8. The medical material needle of claim 6, wherein the middle structure further includes a fourth material, the second material and the fourth material are integrated to wrap the third material of the inner structure in an alternative manner, and the second material and the fourth material are the same or different.

9. The medical material needle of claim 8, wherein the fourth material is a solid material such as a metal or a polymer, or a fluid material such as water or air.

10. The medical material needle of claim 1, wherein the middle structure for wrapping the inner structure includes a plurality of cylindrical or granular structural units in an arrangement having at least one layer.

11. The medical material needle of claim 10, wherein the arrangement of the plurality of cylindrical or granular structural units is cubic stacking, hexagonal stacking or irregular stacking.

12. The medical material needle of claim 1, wherein a contact surface between the outer structure and the middle structure or another contact surface between the middle structure and the inner structure is furnished thereon with micro structures.

13. The medical material needle of claim 1, wherein the inner structure is a hollow cylindrical structure for allowing a fluid to flow thereinside or a wire to pass therethrough.

14. The medical material needle of claim 1, wherein the needle body includes a straight needle, and the three-layer structure is constructed at the straight needle.

15. The medical material needle of claim 1, wherein the needle body includes a plurality of tine needles and a straight needle, the plurality of tine needles are arranged to outside of the straight needle to surround the straight needle, each of the plurality of tine needle is retractable and expandable in a radial direction of the straight needle, and the three-layer structure is constructed at the plurality of tine needles and/or the straight needle.

16. The medical material needle of claim 15, wherein the medical material needle further includes a guide pipe sleeving outside the needle body, and the guide pipe moves axially to retract or expand the plurality of tine needles.

* * * * *